(12) United States Patent
Hepfer et al.

(10) Patent No.: US 6,989,455 B2
(45) Date of Patent: Jan. 24, 2006

(54) TWO-STAGE PROCESS FOR THE HYDROGENATION OF MALEIC ACID TO 1,4-BUTANEDIOL

(75) Inventors: Robert P. Hepfer, St. Charles, IL (US); Craig T. Miller, Batavia, IL (US); Gregory A. Norenberg, Medina, OH (US); Thomas G. Attig, Batavia, IL (US); John R. Budge, Beachwood, OH (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 10/645,429

(22) Filed: Aug. 21, 2003

(65) Prior Publication Data

US 2004/0039213 A1 Feb. 26, 2004

Related U.S. Application Data

(63) Continuation of application No. 09/651,526, filed on Aug. 29, 2000, now abandoned.

(51) Int. Cl.
*C07D 307/02* (2006.01)
*C07D 307/58* (2006.01)
*C07D 307/60* (2006.01)
*C07D 407/00* (2006.01)
*C07C 409/00* (2006.01)

(52) U.S. Cl. ............ 549/508; 549/233; 549/326; 549/295; 568/564; 568/884

(58) Field of Classification Search ........ 549/295, 549/326, 233, 508; 568/864, 884
See application file for complete search history.

(56) References Cited

U.S. PATENT DOCUMENTS

| 5,073,650 | A |   | 12/1991 | Stabel et al. ........... 568/864 |
| 5,196,602 | A | * | 3/1993  | Budge et al. ........... 568/864 |
| 5,698,749 | A | * | 12/1997 | Pedersen et al. ........ 568/864 |
| 5,969,164 | A |   | 10/1999 | Budge et al. ........... 549/508 |
| 6,008,384 | A | * | 12/1999 | Bockrath et al. ........ 549/508 |

FOREIGN PATENT DOCUMENTS

| EP | 0848991 | 6/1998 |
| JP | 73000823 | 1/1973 |

OTHER PUBLICATIONS

Knovel.com/knovel2Searchresults.jsp"Process/Industrial Instruments And Control Handbook".*
"Bonding E-glass to Wood Using a Modified Polyester Resin", Bogner et al., COMPOSITES 2001 Convention and Trade Show; Composites Fabricators Association (CFA); Oct. 4, 2001.

* cited by examiner

Primary Examiner—Taofiq Solola
Assistant Examiner—Ebenezer Sackey
(74) Attorney, Agent, or Firm—William J. Davis; David P. Yusko

(57) ABSTRACT

In the process for the conversion of maleic acid to gamma-butyrolactone, 1.4-butanediol and/or tetrahydrofuran, a feedstream comprising maleic acid is hydrogenated in a first hydrogenation zone to produce a reaction product comprising succinic acid and unreacted hydrogen which is then supplied to a second hydrogenation zone, where succinic acid is converted to 1,4-butanediol, the temperatures of the feedstream comprising maleic acid and the first hydrogenation zone are controlled such that the temperature of maleic acid in the feedstream and the first hydrogenation zone does not exceed about 130° C., thereby minimizing the corrosive effects of the maleic acid and prolonging reactor life and improving overall process economics.

16 Claims, No Drawings

TWO-STAGE PROCESS FOR THE HYDROGENATION OF MALEIC ACID TO 1,4-BUTANEDIOL

This is a continuation of application Ser. No. 09/651,526, filed Aug. 29, 2000, now abandoned.

BACKGROUND OF THE INVENTION

1. Field of the Invention

This invention relates to an process for the hydrogenation of maleic acid to 1.4-butanediol and optionally gamma-butyrolactone and/or tetrahydrofuran. In this process, corrosion of process equipment (e.g. hydrogenation reactors and their internals) is minimized by the use of two hydrogenation zones and by further controlling the temperature of the first hydrogenation reaction zone such that the temperature of maleic acid in the reaction zone does not exceed about 130° C.

2. Description of the Prior Art 1,4-Butanediol is a commercial commodity with a plurality of uses. For example, 1,4-butanediol is used in the production of polybutylene terepthalate and reaction-injected molded (RIM) urethanes.

It is well known that 1,4-butanediol may be obtained by the catalytic hydrogenation of maleic acid, maleic anhydride and similar hydrogenatable compounds. In such processes, aqueous maleic acid is fed with hydrogen to a reactor containing a fixed-bed catalyst. The reaction products containing 1,4-butanediol, tetrahydrofuran and gamma-butyrolactone are then recovered and purified by conventional means.

In part, the invention relates to a two reaction-zone scheme for the production of 1,4-butanediol. U.S. Pat. No. 4,584,419 teaches a process for the hydrogenation of a di-alkyl ester to 1,4-butanediol employing two hydrogenation zones operating in sequence, where the temperature of the second zone is less than the first. U.S. Pat. No. 6,008,384 teaches a two-stage hydrogenation process for the hydrogenation of maleic acid which employs a bimetallic (Ru and Re)-on-carbon catalyst and wherein the effluent of the first-stage is cooled considerably prior to introduction into the second stage. U.S. Pat. No. 5,196,602 teaches a process for the hydrogenation of a maleic anhydride and/or maleic acid to 1,4-butanediol in a two-stage process, operated sequentially, characterized by the use of a different hydrogenation catalysts in the each hydrogenation stage.

More specifically, the invention relates to the manner in which a maleic acid feedstock is hydrogenated to 1,4-butanediol and optionally other products, so as to properly and economically contain said reactions and yield a commercially viable process. To hydrogenate maleic acid to 1 4-butanediol, an elevated temperature is required. For example, U.S. Pat. No. 6,008, 384 teaches that maleic acid is advantageously hydrogenated to 1,4-butanediol at temperatures between 160° C. and 250° C. However, at these temperatures, maleic acid has been observed to be extremely corrosive. Such conditions shorten the expected life of process equipment (e.g. hydrogenation reactors, internals and their auxiliary components), unless specialized metallurgy and/or other costly materials of construction are used. In either event, how the corrosiveness of the maleic acid is addressed in the commercial plant's design, procurement, construction, operation and maintenance has a major impact on process economics of a maleic acid to 1,4-butanediol chemical plant and hence its commercial viability.

A goal of the instant invention is a reactor system configuration and reaction temperature profile which lessens the corrosive effects of the maleic acid feedstock.

SUMMARY OF THE INVENTION

The instant invention is a process for the conversion of maleic acid to at least one of 1,4-butanediol, tetrahydrofuran and gamma-butyrolactone (without specific reference to their secondary by-products, e.g. n-butanol), wherein the process comprises:

(A) a first hydrogenation zone and a second hydrogenation zone connected in series, (B) supplying to the first hydrogenation zone a feedstream comprising maleic acid, (C) reacting in the first hydrogenation zone, the maleic acid feedstock and hydrogen in contact with a catalyst to produce a reaction product comprising succinic acid, (D) supplying to the second hydrogenation zone, the reaction product of the first hydrogenation zone, (E) reacting in the second hydrogenation zone, the reaction product from the first hydrogenation zone and hydrogen in contact with a catalyst to produce a product stream comprising at least one of gamma-butyrolactone, 1,4-butanediol and tetrahydrofuran, and wherein the temperature of the feedstream comprising maleic acid and the temperature of the first hydrogenation zone are controlled such that the temperature of maleic acid in the feedstream and the first hydrogenation zone does not exceed about 130° C., thereby minimizing the corrosive effects of the maleic acid and prolonging the life of the process equipment (e.g. the hydrogenation reactor and its internals and auxiliary components), thereby improving the overall process economics.

In another embodiment, the instant invention is a process for the production of at least one of 1,4-butanediol, tetrahydrofuran and gamma-butyrolactone (without specific reference to their secondary by-products, e.g. n-butanol) which comprises:

(A) a first hydrogenation zone and a second hydrogenation zone connected in series wherein each hydrogenation zone independently contains a hydrogenation catalyst, (B) supplying to the first hydrogenation zone at an inlet temperature of about 70° C. to about 120° C. a feedstream comprising maleic acid, (C) reacting, the feedstream and hydrogen in the first hydrogenation zone to produce reaction product comprising succinic acid and unreacted hydrogen, (D) supplying to the second hydrogenation zone at an inlet temperature of about 130° C. to about 180° C., the reaction product of the first hydrogenation zone, (E) reacting, in the second hydrogenation zone, the reaction product of the first hydrogenation zone and hydrogen to produce product stream comprising at least one of 1,4-butanediol, tetrahydrofuran and gamma-butyrolactone.

In another embodiment of the instant invention, heat is added to the reaction product from the first hydrogenation zone to raise the temperature of the reaction product of the first hydrogenation zone to a temperature above about 130° C. prior to supplying the reaction product to the second hydrogenation zone.

DETAILED DESCRIPTION OF THE INVENTION

The instant invention is a process for the hydrogenation of maleic acid to at least one of 1,4-butanediol, tetrahydrofuran and gamma-butyrolactone. Typically, this reaction is conducted in a single hydrogenation reactor system. However, since the maleic acid is very corrosive at reaction temperatures, significant corrosion is visible in reactors constructed of conventional (i.e., carbon steel) materials.

While not intending to be bound by theory it is believed that the reaction of maleic acid to 1,4-butanediol proceeds through at least two intermediates as follows:

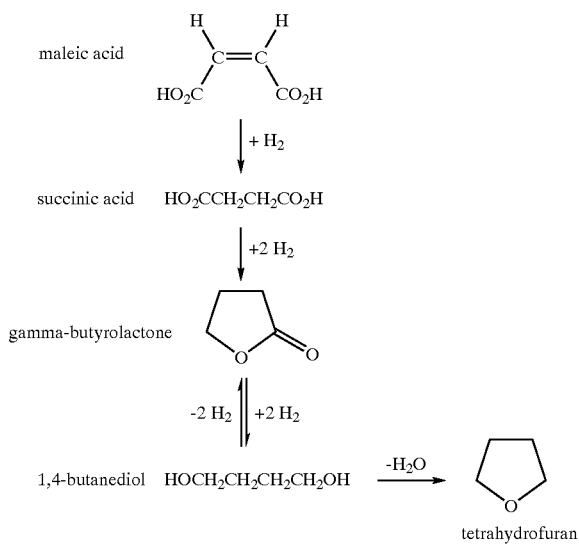

Without further elaboration, gamma-butyrolactone, 1,4-butanediol and tetrahydrofuran are reaction products and by the addition/subtraction of hydrogen and/or water one product is converted to another. Further, by adjusting the operating parameters of the second hydrogenation zone, the product slate may be altered to produce varying ratios of 1,4-butanediol, tetrahydrofuran and gamma-butyrolactone. Typically, 1,4-butanediol is the preferred product of the instant process.

As stated earlier, it has been observed that maleic acid is very corrosive at temperatures exceeding approximately 140° C. It has also known (i) that the hydrogenation of maleic acid to succinic acid proceeds at acceptable rates at lower temperatures than required for the hydrogenation of succinic acid to 1,4-butanediol, and (ii) that succinic acid is much less corrosive than maleic acid at such elevated temperatures.

These items coupled with the desire to minimize the corrosive effects of the maleic acid has led to the discovery that the conversion of maleic acid to 1,4-butanediol is more beneficially conducted in two, separately distinct reaction stages or zones, wherein the first stage is operated at a temperature below about 130° C., preferably below about 120° C., to convert the maleic acid to succinic acid and then the temperature of the second stage is operated at a temperature above about 130° C. to convert the succinic acid to at least one of gamma-butyrolactone, 1,4-butanediol and tetrahydrofuran. More specifically, maleic acid is supplied to a first hydrogenation zone at a temperature of about 70° C. to about 120° C. and is then hydrogenated to succinic acid. The reaction temperature in the first hydrogenation zone is controlled such that the effluent from the first hydrogenation zone does not exceed a temperature of about 130° C. Preferably, inlet and reactor temperatures are controlled in the first hydrogenation zone such that the maleic acid does not exceed about 120° C. more preferably such that the maleic acid does not exceed 100° C. The succinic acid from the first hydrogenation zone is then routed to the second hydrogenation zone at a temperature of 130° C. to about 180° C., (heat is added to this stream, if necessary) where it is hydrogenated in the second hydrogenation zone to at least one of gamma-butyrolactone, 1,4-butanediol and tetrahydrofuran. Since maleic acid is not present in a reactor at elevated temperatures (ideally no maleic acid at approximately 100° C. and above), the corrosive effects of the maleic acid are significantly minimized, thereby prolonging the life of the hydrogenation reactor(s) and any other affected process equipment and improving the overall process economics (capital, operating and maintenance costs).

Reactants

In the process of the instant invention, maleic acid is reacted with a hydrogen-containing gas in the presence of the catalyst. Other hydrogenatable precursors may be combined with the maleic acid feedstock. A "hydrogenatable precursor" is any carboxylic acid or anhydride thereof, carboxylic acid ester, lactone or mixtures thereof which, when hydrogenated, produces gamma-butyrolactone, 1,4-butanediol and tetrahydrofuran. Representative hydrogenatable precursors include: maleic anhydride, fumaric acid, succinic anhydride, succinic acid, succinate esters such as the $C_1$ to $C_8$ dialkyl succinates (e.g. dimethyl succinate), maleate esters such as the $C_1$ to $C_8$ dialkyl maleates (e.g. dimethyl maleate), gamma-butyrolactone or mixtures thereof. As used herein, "maleic acid feedstock" shall refer to the process feed comprising maleic acid, other hydrogenatable precursors, water or other suitable solvents.

Maleic acid which is typically obtained by reacting n-butane or benzene in an oxygen-containing gas in the presence of a catalyst (typically a mixed oxide of vanadium and phosphorus) to oxidize in the vapor phase the n-butane or benzene to maleic anhydride, and then collecting the maleic anhydride by a water quench to produce maleic acid in an aqueous solution. The maleic acid concentrations of such solutions is in the range of 10 to 60 percent by volume. The oxidation of n-butane or benzene is typically operated at a temperature of about 300° C. to 600° C. and a pressure of about 0.5 to 20 atmospheres (50 to 2000 kPa).

Typically, the hydrogen-containing gas is commercially pure hydrogen with no diluent gases. However, the hydrogen containing gas in addition to hydrogen ($H_2$) may also contain nitrogen ($N_2$), any gaseous hydrocarbons (e.g. methane), as well as gaseous oxides of carbon (e.g. carbon monoxide and carbon dioxide). Preferably, a stoichiometric excess of hydrogen (i.e. more hydrogen than required for the complete conversion of the maleic acid to 1,4-butanediol) is employed in the process to ensure reaction completeness and aid in temperature control. Typically, the hydrogen is combined with the maleic acid feedstock prior to introduction to the first hydrogenation zone. The reaction product and unreacted hydrogen is then fed to the second hydrogenation zone. Alternatively, the hydrogen may be fed directly to the first hydrogenation zone, or fed the simultaneously to each hydrogenation zone.

Catalyst

The catalysts employed in the instant invention are any catalyst useful for the hydrogenation of maleic acid to 1,4-butanediol. Typically, the catalyst comprises a noble metal of Group VIII of the Periodic Table selected from the group consisting of at least one of palladium, ruthenium, rhodium, osmium, iridium and platinum. These include (i) catalysts also containing at least one of rhenium, manganese or tellurium as described in UK Patent Publication No. 01551741, (ii) catalysts also containing at least one of silver and gold as described in U.S. Pat. No. 4,096,156, (iii) catalysts also containing at least one metal capable of alloying with the noble Group VIII metal and at least one of rhenium, tungsten or molybdenum as described in U.S. Pat. No. 5,149,680, and (iv) catalysts also containing silver and rhenium and at least one iron, aluminum and cobalt as described in U.S. Pat. No. 5,969,164. Examples of other suitable catalyst include palladium and rhenium on a carbon support as described in UK Patent Publication No. 01543232 and U.S. Pat. No. 4,659,686. Such catalysts may be prepared by the techniques described in the listed patents as well as by the techniques described in U.S. Pat. Nos. 5,473,086 and 5,698,749. These catalyst compositions may also be further modified through the incorporation of a metal or metals selected from Groups IA, IIA or VIII.

The preferred catalysts employed in the instant invention for the first hydrogenation zone comprise palladium supported on carbon and for the second hydrogenation zone comprise palladium, silver and rhenium supported on carbon. More preferably such second hydrogenation zone catalysts contain additionally at least one of iron, cobalt and aluminum. The carbons for use in this invention have a BET (define) surface area of at least 200 $m^2/g$, and preferably be in the range of 500–1500 $m^2/g$. Catalysts of this type are described in U.S. Pat. No. 5.149,680.

In the instant invention a first hydrogenation zone and a second hydrogenation zone are connected in series and each hydrogenation zone contains a catalyst. The same or different catalysts may be used in each zone. The predominant reaction in the first hydrogenation zone (i.e. maleic acid to succinic acid) is more facile then the predominant reactions in the second hydrogenation zone (i.e. succinic acid through to 1,4-butanediol). As such, the catalysts employed in each zone may be selected, so as to optimize both the technical performance and production economics for each zone.

The Process

The method for carrying out the process comprises reacting a maleic acid-containing feedstock with a hydrogen-containing gas in the presence of a hydrogenation catalyst, and recovering and purifying the reaction products by distillation. The reaction is conducted in the liquid phase in two hydrogenation zones operated or connected in series.

In the practice of the instant invention, the two hydrogenation zones can be combined into a single reactor system or each hydrogenation zone can comprise one or more reactor systems. Typically, each hydrogenation zone comprises a single, fixed-bed reactor. However, other conventional apparatus and techniques, such as agitated slurry reactors, which can accommodate the temperature, pressure and contact times required for the instant process for may be employed. Optionally, multiple-stage reactors may be employed in each hydrogenation zone. The process may be operated in batch or continuous mode. The amount of catalyst required in each hydrogenation zone will vary widely and is dependent upon a number of factors, such as reactor size and design, contact time and the like.

Liquid maleic acid feedstock is fed to the top of the first zone. The maleic acid feedstock is fed continuously at concentrations ranging from dilute solutions to near the maximum solubility level. The feedstock may contain about 10 to about 60 weight percent maleic acid (or other hydrogenatable precursor) with the higher concentrations being more economical for commercial applications and preferred due to less water to recycle or dispose. Preferably the precursor solution contains about 20 to about 50 weight percent maleic acid (or other hydrogenatable precursor).

The hydrogen-containing gas is also fed continuously to the first hydrogenation zone. Typically, the hydrogen is combined with the maleic acid feedstock prior to the introduction of the feedstock into the first hydrogenation zone. Alternatively the hydrogen may be fed directly to the first hydrogenation zone, or fed simultaneously to each hydrogenation zone. Typically, the amount of hydrogen is in considerable stoichiometric excess to the other reactants to ensure suitable hydrogen partial pressure effects for reactions to proceed to desired end-products.

In the first hydrogenation zone maleic acid is reacted with hydrogen to produce succinic acid. More specifically, maleic acid is supplied to a first hydrogenation zone at a temperature of about 70° C. to about 120° C. and is then hydrogenated to succinic acid. The reaction temperature in the first hydrogenation zone is controlled such that the effluent from the first hydrogenation zone does not exceed a temperature of about 130° C., preferably 120° C. More preferably, the temperatures of the feedstream comprising maleic acid and the first hydrogenation zone are controlled such that the temperature of maleic acid in the feedstream and the first hydrogenation zone does not exceed about 100° C. Even lower feedstream and reaction temperatures for the first hydrogenation zone are possible and preferred as long as sufficient conversion of maleic acid to succinic acid is maintained. The first hydrogenation zone is operated at a pressure of about 1000 psig to about 4,500 psig (approximately about 65 atmospheres to about 300 atmospheres), preferably about 100 to 270 atmospheres, with hydrogen to hydrogenatable precursor ratios ($H_2/P$) of between 5 to 1 and 1000 to 1 and contact times of about 0.1 minutes to about 20 hours.

The effluent from the first hydrogenation zone, predominately succinic acid, unreacted hydrogen and water (from the maleic acid feedstock) is fed continuously to the second hydrogenation zone, wherein the succinic acid reacts with hydrogen (passing through one or more intermediates) to produce a reaction product composed predominantly of 1,4-butanediol and optionally tetrahydrofuran and gamma-butyrolactone.

The reaction product of the first hydrogenation zone is supplied to the second hydrogenation zone at a temperature at or above about 130° C., more typically between about 130° C. to about 180° C. Heat is added to the reaction product from the first hydrogenation zone to safely raise this reaction product to a temperature of about 130° C. to about 180° C. prior to supplying the reaction product from the first hydrogenation zone to the second hydrogenation zone. The reaction temperature in the second hydrogenation zone is controlled such that the reactor effluent from the second hydrogenation zone comprising 1,4-butanediol does not exceed a temperature of about 180° C. Operating the second hydrogenation zone to maintain an effluent temperature at less than about 180° C. will preferentially produce 1,4- butanediol and minimize the formation of tetrahydrofuran. Additionally, the second hydrogenation zone is operated at a pressure of about 1000 psig to about 4,500 psig (approximately about 65 atmospheres to about 300 atmospheres) preferably about 100 to about 270 atmospheres, with hydrogen to hydrogenatable precursor ratios ($H_2/P$) of between 5 to 1 and 1000 to 1 and contact times of about 0.1 minutes to about 20 hours. The effluent from the second hydrogenation zone, predominately 1,4-butanediol, unreacted hydrogen and water with minor quantities of tetrahydrofuran, gamma-butyrolactone and other by-products.

Unreacted hydrogen is separated and recycled to the first hydrogenation zone or combined with the maleic acid feedstock. The 1,4-butanediol is recovered and purified by fractional distillation. By-products which are formed in small amounts or unreacted feed, such as succinic acid, are optionally returned to the hydrogenation stage, preferably the second hydrogenation zone. Gamma-butyrolactone may also be recycled to the first and/or second hydrogenation zones, preferably to the second hydrogenation zone.

Using the process of this invention, more specifically using the hydrogenation catalyst and operating parameters described herein, maleic acid is converted virtually quantitatively in a simple reaction. The yields of 1,4-butanediol achieved are about 80 mole percent or greater, typically about 90 mole percent or greater. Significantly, the formation of non-utilizable by-products is slight.

EXAMPLES

Several tests were conducted in a 200 cc reactor containing 4%Pd/4%Ag/4%Re on carbon catalyst. Aqueous maleic acid solutions (22 and 44 w/v%) and vaporous hydrogen were fed to the reactors. Corrosion test rods of various metal compositions were placed inside the catalyst bed, including several Hastelloy alloys, titanium grade 7, Zirconium 7202 and 316L stainless steel. The reactors were operated at various temperatures to convert the feed materials to a reaction product comprising succinic acid, gamma-butyrolactone and/or 1,4-butanediol. It was noted that at higher temperature runs, evidence of corrosion existed on the test rods. An analysis of the test rods and data from the several runs (for example, comparing the reaction temperatures for the test runs with corrosion on the test rods versus test runs with no corrosion, and for the test runs with corrosion on the test rods comparing internal reactor temperature plots, i.e. temperature vs. bed height, to the location of the corrosion on the test rods) revealed that corrosion on the test rods occurred when and where the test rods were exposed to maleic acid at temperatures above approximately 140° C. It was further noted that when portions of the catalyst bed were exposed to maleic acid at temperatures not exceeding approximately 130° C. that corrosion on the test rods was essentially eliminated.

It is to be understood that the subject invention is not to be limited by the exact description set forth herein. These have been provided merely to demonstrate operability, and the selection of catalysts, process equipment metallurgies, carbon supports, process stream concentrations, contact times, solids loadings, feedstocks, reaction conditions, and products, if any, can be determined from the total specification disclosure provided, without departing from the spirit of the invention herein disclosed and described, the scope of the invention including modifications and variations that fall within the scope of the attached claims.

The claimed invention is:

1. A continuous process for the production of at least one of gamma-butyrolactone, 1,4-butanediol and tetrahydrofuran comprising:
   (A) a first hydrogenation zone and a second hydrogenation zone connected in series,
   (B) supplying to the first hydrogenation zone a feedstream comprising maleic acid,
   (C) reacting in the first hydrogenation zone, the maleic acid feedstock and hydrogen in contact with a catalyst to produce a reaction product comprising succinic acid,
   (D) supplying to the second hydrogenation zone, the reaction product of the first hydrogenation zone,
   (E) reacting in the second hydrogenation zone, the reaction product from the first hydrogenation zone and hydrogen in contact with a catalyst to produce a product stream comprising at least one of gamma-butyrolactone, 1,4-butanediol and tetrahydrofuran,
   wherein the temperature of the feedstream comprising maleic acid and the temperature of the first hydrogenation zone are controlled such that the temperature of maleic acid in the feedstream and the first hydrogenation zone does not exceed about 130° C.

2. The process of claim 1, wherein the temperature of the feedstream comprising maleic acid and the temperature of the first hydrogenation zone are controlled such that the temperature of maleic acid in the feedstream and the first hydrogenation zone does not exceed about 120° C.

3. The process of claim 1, wherein the temperature of the feedstream comprising maleic acid and the temperature of the first hydrogenation zone are controlled such that the temperature of maleic acid in the feedstream and the first hydrogenation zone does not exceed about 100° C.

4. The process of claim 1, wherein heat is added to the reaction product from the first hydrogenation zone to raise the reaction product to a temperature above about 130° C. prior to supplying the reaction product from the first hydrogenation zone to the second hydrogenation zone.

5. The process of claim 1, wherein heat is added to the reaction product from the first hydrogenation zone to raise the reaction product to a temperature of about 130° C. to about 180° C. prior to supplying the reaction product from the first hydrogenation zone to the second hydrogenation zone.

6. The process of claim 1, wherein the feedstream comprises maleic acid and at least one other hydrogenatable precursor.

7. The process of claim 6, wherein the hydrogenatable precursor is at least one of maleic anhydride, succinic acid, succinic anhydride, succinate esters, maleate esters, or gamma-butyrolactone.

8. The process of claim 1, wherein the ratio of hydrogen to maleic acid supplied to the process is between about 5 to 1 and about 1000 to 1.

9. The process of claim 1, wherein the operating pressure in each hydrogenation zone is independently between about 65 and about 300 atmospheres.

10. The process of claim 1, wherein the operating pressure in each hydrogenation zone is independently between about 100 and about 270 atmospheres.

11. The process of claim 1, wherein the contact time in each hydrogenation zone is independently between about 0.1 minutes and 20 hours.

12. A continuous process for the production of at least one of gamma-butyrolactone, 1,4-butanediol and tetrahydrofuran comprising:

(A) a first hydrogenation zone and a second hydrogenation zone connected in series, (B) supplying to the first hydrogenation zone at an inlet temperature of about 70° C. to about 120° C. a feedstream comprising maleic acid, wherein the temperature of maleic acid in the feedstream and the first hydrogenation zone does not exceed about 130° C., (C) reacting in the first hydrogenation zone, the maleic acid feedstock and hydrogen in contact with a catalyst to produce a reaction product comprising succinic acid, (D) supplying to the second hydrogenation zone at an inlet temperature of about 130° C. to about 180° C., the reaction product of the first hydrogenation zone, (E) reacting in the second hydrogenation zone, the reaction product from the first hydrogenation zone and hydrogen in contact with a catalyst to produce a product stream comprising at least one of gamma-butyrolactone, 1,4-butanediol and tetrahydrofuran.

13. A continuous process for the production of at least one of gamma-butyrolactone, 1,4-butanediol and tetrahydrofuran comprising:

(A) a first hydrogenation zone and a second hydrogenation zone connected in series therewith wherein each hydrogenation zone independently contains a catalyst comprising a noble metal of Group VIII, (B) supplying to the first hydrogenation zone at an inlet temperature of about 70° C. to about 120° C. a feedstream comprising maleic acid, wherein the temperature of maleic acid in the feedstream and the first hydrogenation zone does not exceed about 130° C., (C) reacting in the first hydrogenation zone, the maleic acid feedstock and hydrogen in contact with a catalyst to produce a reaction product comprising succinic acid and unreacted hydrogen, (D) supplying to the second hydrogenation zone at an inlet temperature of about 130° C. to about 180° C., the reaction product of the first hydrogenation zone, (E) reacting in the second hydrogenation zone, the reaction product from the first hydrogenation zone and hydrogen in contact with a catalyst to produce a product stream comprising 1,4-butanediol.

14. The process of claim 13, wherein the noble metal of Group VIII for the catalysts in the first hydrogenation zone and the second hydrogenation zone are independently selected from the group consisting of palladium, platinum, rhodium and ruthenium.

15. The process of claim 13, wherein the catalyst in the first hydrogenation zone and the catalyst in the second hydrogenation zone, each comprise palladium.

16. The process of claim 13, wherein the catalyst in the first hydrogenation zone comprises palladium on a carbon support and the catalyst in the second hydrogenation zone comprises palladium, rhenium and silver on a carbon support.

* * * * *